US011719710B2

(12) United States Patent
Horsch et al.

(10) Patent No.: US 11,719,710 B2
(45) Date of Patent: Aug. 8, 2023

(54) GDF-15 AND/OR TROPONIN T FOR PREDICTING KIDNEY FAILURE IN HEART SURGERY PATIENTS

(71) Applicant: Roche Diagnostics Operations, Inc., Indianapolis, IN (US)

(72) Inventors: Andrea Horsch, Mannheim (DE); Dietmar Zdunek, Tutzing (DE); Georg Hess, Mainz (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 156 days.

(21) Appl. No.: 16/695,713

(22) Filed: Nov. 26, 2019

(65) Prior Publication Data
US 2020/0200771 A1 Jun. 25, 2020

Related U.S. Application Data

(63) Continuation of application No. 14/856,543, filed on Sep. 16, 2015, now abandoned, which is a continuation of application No. 13/525,330, filed on Jun. 17, 2012, now abandoned, which is a continuation of application No. PCT/EP2010/070058, filed on Dec. 17, 2010.

(30) Foreign Application Priority Data

Dec. 18, 2009 (EP) .................................... 09179925

(51) Int. Cl.
G01N 33/74 (2006.01)
G01N 33/68 (2006.01)
A61P 13/12 (2006.01)
C07K 14/47 (2006.01)

(52) U.S. Cl.
CPC ......... G01N 33/74 (2013.01); C07K 14/4716 (2013.01); G01N 33/6863 (2013.01); G01N 33/6893 (2013.01); G01N 2333/4712 (2013.01); G01N 2333/495 (2013.01); G01N 2333/52 (2013.01); G01N 2800/347 (2013.01); G01N 2800/50 (2013.01); G01N 2800/52 (2013.01)

(58) Field of Classification Search
CPC .. G01N 33/68; G01N 33/74; G01N 2800/347; G01N 2800/50; G01N 2800/52
See application file for complete search history.

(56) References Cited

U.S. PATENT DOCUMENTS 5,744,305 A 4/1998 Fodor et al.
2007/0248989 A1 10/2007 Devarajan

FOREIGN PATENT DOCUMENTS

| EP | 0 648 228 B1 | 11/1998 | |
| EP | 1 983 345 A1 | 10/2008 | |
| EP | 1983345 A1 * | 10/2008 | ......... G01N 33/6893 |
| WO | WO 1999/006445 A1 | 2/1999 | |
| WO | WO 2000/070051 A1 | 11/2000 | |
| WO | WO 2002/083913 A1 | 10/2002 | |
| WO | WO 2002/089657 A1 | 11/2002 | |
| WO | WO 2005/113585 A2 | 12/2005 | |
| WO | WO 2008/060607 A2 | 5/2008 | |
| WO | WO 2009/083950 A3 | 7/2009 | |
| WO | WO 2009/141357 A1 | 11/2009 | |

OTHER PUBLICATIONS

Wollert et al., Clin. Chem., 2017, vol. 63(1): 140-151.*
Wallin et al., Br. J. Cancer, 2011, vol. 104(10):1619-1627.*
Massoudy et al., Nephrol. Dial. Transplant., 2008, vol. 23(9):2853-2860.*
Hetland et al., Clinical Chemistry, 1998, vol. 44(6):1348-1350.*
Giannitsis et al., "Analytical validation of a high-sensitivity cardiac troponin T assay " Clin. Chem., 56(2):254-61 (Feb. 2010; Epub Dec. 3, 2009).
Cheng et al., "Wild-type p53 attenuates cancer cell motility by inducing growth differentiation factor-15 expression." Endocrinology, 152(8):2987-95 (Aug. 2011; Epub May 17, 2011).
International Search Report dated May 12, 2011 in International Application No. PCT/EP2010/070058, 7 pages.
Bellomo, R. et al., "The pathophysiology of cardiac surgery-associates acute kidney injury (DSA-AKI)", The International Journal of Artificial Organs, 2008, pp. 166-176, vol. 31, No. 2.
Brincat, Stephan and Hilton, Rachel, "Prevention of acute kidgney injury", British Journal of Hospital Medicine, Aug. 2008, pp. 450-454, vol. 69, No. 8.
Ejaz et al., "Uric Acid: A Novel Risk Factor for Acute Kidney Injury in High-Risk Cardiac Surgery Patients?" American Journal of Nephrology, 2009, pp. 425-429, vol. 30.
Haase, et al., "Novel Biomarkers Early Predict the Severity of Acute Kidney Injury After Cardiac Surgery in Adults", The Annals of Thoracic Surgery, 2009, pp. 124-130, vol. 88.
Liangos, et al., "Comparative analysis of urinary biomarkers for early detection of acute kidney injury following cariopulmonary bypass", Biomarkers, 2009, pp. 423-431, vol. 14, No. 6.
Mehta, et al., "Bedside Tool for Predicting the Risk of Postoperative Dialysis in Patients Undergoing Cardiac Surgery", Circulation, 2006, pp. 2208-2216, vol. 114.
Portilla, et al., "Liver fatty acid-binding protein as a biomarker of acute kidney injury after cardiac surgery", Kidney International, 2008, pp. 465-472, vol. 73.
Zimmers, et al., "Growth Differentiation Factor-15/Macrophage Inhibitory Cytokine-1 Induction After Kidney and Lung Injury", Shock, 2005, pp. 543-548, vol. 23, No. 6.
Abelha et al., "Determinants of postoperative acute kidney injury" Critical Care, 13(R79):10 pages (2009).

(Continued)

Primary Examiner — Xiaozhen Xie
(74) Attorney, Agent, or Firm — McDonnell Boehnen Hulbert & Berghoff LLP

(57) ABSTRACT

The present disclosure relates to the field of laboratory diagnostics. Specifically, means and methods are disclosed for determining a patient's risk of suffering from acute kidney injury after a surgical procedure based on the detection of GDF-15, troponin T and/or a natriuretic peptide.

9 Claims, No Drawings

(56) References Cited

OTHER PUBLICATIONS

Anderson et al., "Molecular Basis of Human Cardiac Troponin T Isoforms Expressed in the Developing, Adult, and Failing Heart" Circulation Research, 1995, pp. 681-686, vol. 76.
Baek et al., "Cyclooxygenase Inhibitors Regulate the Expression of a TGF-beta Superfamily Member That has Proapoptotic and Antitumorigenic Activities" Molecular Pharmacology, 2001, pp. 901-908, vol. 59, No. 4.
Bartels et al., "Serum Kreatininbestimmung Ohne Enteiseissen" Clinica Chimica Acta, 1972, pp. 193-197, vol. 7, English Abstract provided.
Bauskin et al., "The propeptide of macrophage Inhibitory cytokine (MIC1), a TGF-B super-family member, acts as a quality control determinant for correctly folded MIC-1" EMBO 2000, pp. 2212-2220, vol. 19 No. 10.
Bhayana, Vipin et al., Discordance Between Results for Serum Troponin T and Troponin I in Renal Disease, Clinical Chemistry, 1995, pp. 312-317, vol. 41, No. 2.
Bonow, Robert O., New Insights Into the Cardiac Natriuretic Peptides, Circulation, 1996, pp. 1946-1950, vol. 93.
Brown, Jeremiah R. et al., Long-Term Survival After Cardiac Surgery is Predicted by Estimated Glomerular Filtration Rate, Annals of Thoracic Surgery, 2008, pp. 4-12, vol. 86.
Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.
De Zoysa, Janak R., Cardiac troponins and renal disease, Nephrology, 2004, pp. 83-88, vol. 9.
Eagle, Kim A. et al., ACC/AHA Guidelines for Coronary Artery Bypass Graft Surgery A Report of the American College of Cardiology/ American Heart Association Task Force on Practice Guidelines (Committee to Revise the 1991 Guidelines for Coronary Artery Bypass Graft Surgery), Circulation, 2004, pp. e340-e437, vol. 110, No. 14.
Eagle, Kim A. et al., ACC/AHA Guidelines for Coronary Artery Bypass Graft Surgery A Report of the American College of Cardiology/ American Heart Association Task Force on Practice Guidelines (Committee to Revise the 1991 Guidelines for Coronary Artery Bypass Graft Surgery), Journal of the American College of Cardiology, 1999, pp. 1262-1347, vol. 14, No. 4.
European Search Report dated Aug. 31, 2017, in Application No. EP 17179543.8, 16 pages.
Ferrieres, Gaelle et al., Human cardiac troponin I: precise identification of antigenic epitopes and prediction of secondary structure, Clinical Chemistry, 1998, pp. 487-493, vol. 44, No. 3.
Foster-Swanson, A. et al., Reference Interval Studies of the Rate-Blanked Creatinine/JafféMethod on BM/Hitachi Systems in Six U.S. Laboratories, Clinical Chemistry, 1994, p. 1057, Abstract 0361, vol. 40, No. 6.
Hanley, James A. and McNeil, Barbara J., The Meaning and Use of the Area under a Receiver Operating Characteristic (ROC) Curve, Radiology, 1982, pp. 29-36, vol. 143.

Hromas, Robert et al., PLAB, a novel placental bone morphogenetic protein, Biochimica et Biophysica Acta, 1997, pp. 40-44, vol. 1354.
Kempf, Tibor et al., The Transforming Growth Factor-β Superfamily Member Growth-Differentiation Factor-15 Protects the Heart From Ischemia/Reperfusion Injury, Circulation Research, 2006, pp. 351-360, vol. 98.
Lawton, Lee N. et al., Identification of a novel member of the TGF-beta superfamily highly expressed in human placenta. Gene, 1997, pp. 17-26, vol. 203.
Mohammed, Asim A. et al., Prospective, Comprehensive Assessment of Cardiac Troponin T Testing After Coronary Artery Bypass Graft Surgery, Circulation, 2009, pp. 843-850, vol. 120.
Morrish, D. W. et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.
Mueller, Thomas et al., Long-term stability of endogenous B-type natriuretic peptide (BNP) and amino terminal proBNP (NT-proBNP) in frozen plasma samples, Clinical Chemistry & Laboratory Medicine, 2004, pp. 942-944, vol. 42, No. 8.
Needleman, Saul B. and Wunsch, Christian D., A General Method Applicable to the Search for Similarities in the Amino Acid Sequence of Two Proteins, Journal of Molecular Biology, 1970, pp. 443-453, vol. 48.
Nolan, John P. and Sklar, Larry A., Suspension array technology: evolution of the flat-array paradigm, TRENDS in Biotechnology, 2002, pp. 9-12, vol. 20, No. 1.
Paralkar, Vishwas M. et al., Cloning and Characterization of a Novel Member of the Transforming Growth Factor-β/Bone Morphogenetic Protein Family, The Journal of Biological Chemistry, 1998, pp. 13760-13767, vol. 273, No. 22.
Pearson, William R. and Lipman, David J., Improved tools for biological sequence comparison, Proceedings of the National Academy of Sciences USA, 1988, pp. 2444-2448, vol. 85.
Seelig, H. P. and Wüst, H., Die Kreatinbestimmung mitder JafféReaktion, Ärztliches Labor, 1969, pp. 34-39, English Summary, vol. 15.
Smith, M. W. et al., Delayed metabolism of human brain natriuretic peptide reflects resistance to neutral endopeptidase. Journal of Endocrinology, 2000, pp. 239-246, vol. 167.
Smith, Temple F. and Waterman, Michael S., Comparison of Biosequences, Advances in Applied Mathematics, 1981, pp. 482-489, vol. 2.
Song, Young Rim et al., Prevention of Acute Kidney Injury by Erythropoietin in Patients Undergoing Coronary Artery Bypass Grafting: A Pilot Study, American Journal of Nephrology, 2009, pp. 253-260, vol. 30.
Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.
Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.

* cited by examiner

GDF-15 AND/OR TROPONIN T FOR PREDICTING KIDNEY FAILURE IN HEART SURGERY PATIENTS

PRIORITY CLAIM

This application is a continuation of U.S. application Ser. No. 14/856,543, filed Sep. 16, 2015, now abandoned, which is a continuation of U.S. application Ser. No. 13/525,330, filed Jun. 17, 2012, now abandoned, which is a continuation of International Application No. PCT/EP2010/070058, filed Dec. 17, 2010, which claims the benefit of European Patent Application No. 09179925.4, filed Dec. 18, 2009, the disclosures of each of which are explicitly incorporated by reference in their entirety.

FIELD OF THE DISCLOSURE

The present disclosure relates to the field of laboratory diagnostics.

BACKGROUND OF THE DISCLOSURE

GDF-15 is a member of the TGF beta family; it is synthesized as a 40 kD propeptide and undergoes cleavage of its N-terminal moiety to generate an active 30 kD disulfide-linked dimeric protein that is secreted. GDF-15 has been linked to heart failure and to cardiac reperfusion injury (Kempf et al., 2006, Cir. Res. 98(3): 351-60). GDF-15 has been shown to be induced in many tissues in response to various stresses.

Troponin T is a part of the contractile apparatus of cardiomyocytes. It is a well established biomarker of myocardial necrosis or damage. In line with these findings, it has been shown that elevated troponin T levels measured within 24 hours after coronary artery bypass graft surgery indicate an increased risk of postoperative complications (Mohammed et al., 2009, Circulation 120(10): 843-50).

Patients with advanced cardiovascular atherosclerosis benefit from percutaneous cardiovascular intervention (PCI), as summarized by the ACC/AHA guidelines for Revascularization with PCI and coronary artery bypass graft surgery (CABG) in patients with stable angina (Eagle et al., 2004, Circulation 110(14): e340-437).

Coronary bypass surgery, however, is associated with a significant risk of complications. For example, the incidence of acute kidney injury (AKI) after coronary bypass surgery ranges from 10 to 20% (Mehta et al., 2006, Circulation 114(21): 2208-16). In addition, 1% to 5% of individuals undergoing coronary bypass surgery require postoperative dialysis. The pathogenesis of postoperative AKI appears multifactorial and its association with increased morbidity and long term mortality after cardiac surgery is well established (Brown et al., 2008, Ann. Thorac. Surg. 86(1): 4-11).

AKI may be prevented in at-risk patients. Preventive measures include careful fluid balance during and after surgery, avoidance of low cardiopulmonary bypass (CPB) perfusion temperatures, avoidance of nephrotoxic drugs prior to surgery, and application of drugs such as erythropoietin after surgery (Song et al., 2009, Am. J. Nephrol. 30(3): 253-60).

Therefore, it is of high importance to identify individuals at risk of complications before cardiovascular surgery to avoid risk factors that might lead to AKI. Moreover, in at-risk individuals, careful follow up of kidney function after surgery is indicated.

Consequently, the technical problem underlying the present disclosure could be seen as the provision of means and methods for identifying individuals that have an elevated risk of acute kidney injury after a surgical procedure. The problem is solved by the embodiments of the present disclosure described in the claims and in the specification below.

SUMMARY OF THE DISCLOSURE

The present disclosure relates to the field of laboratory diagnostics. Specifically, means and methods are disclosed for determining the risk of acute kidney injury in a patient following a surgical procedure by determining the amount of GDF-15, troponin, and/or natriuretic peptide.

Thus, the present disclosure relates to a method for predicting the risk of acute kidney injury (AKI) in an at-risk patient subjected to a surgical procedure, comprising the steps of determining the amount of GDF-15, troponin, and/or natriuretic peptide in a sample obtained from the patient; and comparing the amount of GDF-15, troponin T, and/or natriuretic peptide in the sample with a suitable reference amount, whereby the risk of AKI in the at-risk patient is predicted.

The present disclosure also relates to a method for predicting the risk of AKI in an at-risk patient subjected to a surgical procedure, comprising the step of comparing the amount of GDF-15, troponin, and/or natriuretic peptide determined in a sample obtained from the patient with a suitable reference amount, whereby the risk of AKI is predicted.

The present disclosure further relates to in vitro methods for predicting the risk of AKI in an at-risk patient subjected to a surgical procedure based on the biomarker GDF-15, troponin, and/or natriuretic peptide. Such methods may comprise steps in addition to those described above, including steps for sample pre-treatment or evaluation of results obtained by the method.

The methods of the present disclosure may be carried out manually or may be automated. One or more steps of the disclosed methods may be automated, e.g., by suitable robotic and sensory equipment for determining the amount of GDF-15, troponin, and/or natriuretic peptide in a patient sample, or by a computer-implemented step of comparing the amount of GDF-15, troponin, and/or natriuretic peptide determined in a sample from a patient with a suitable reference amount.

The above-described embodiments of the various aspects of the disclosure may be used alone or in any combination thereof without departing from the scope of the disclosure.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The term "predicting the risk" as used herein refers to assessing the probability that a subject will suffer from acute kidney injury within a certain time window, i.e., the predictive window. In accordance with the present disclosure, the predictive window may be within 1 day, 2 days, or 3 days after completion of the intervention. The endpoint of acute kidney injury within the predictive window will become apparent by an increase of the serum creatinine as described herein. However, as will be understood by those skilled in the art, such an assessment is usually not intended to be correct for 100% of the subjects to be investigated. The term, however, requires that a prediction can be made for a statistically significant portion of subjects in a proper and correct manner. Whether a portion is statistically significant can be determined by those skilled in the art using various well known statistic evaluation tools, e.g., determination of confidence intervals, p-value determination, Student's t-test, and Mann-Whitney test. Details regarding suitable statistic evaluation tools can be found in Dowdy and Wearden, Statistics for Research (John Wiley & Sons, New York 1983). Suitable confidence intervals are at least 90%, at least 95%, at least 97%, at least 98%, or at least 99%. Suitable p-values are 0.1, 0.05, 0.01, 0.005, or 0.0001. In one embodiment of the disclosed methods, the probability envisaged by the present disclosure allows that the prediction of an increased, normal, or decreased risk will be correct for at least 60%, at least 70%, at least 80%, or at least 90% of the subjects of a given cohort or population. Predictions of risk in the disclosed methods relate to predicting whether or not there is an increased risk for acute kidney injury compared to the average risk for developing acute kidney injury in a population of subjects rather than giving a precise probability for the risk.

An "at-risk patient" according to the present disclosure is a patient who will suffer from acute kidney injury following a surgical procedure, with a statistically significant increased probability compared to the incidence of said acute kidney injury in a population of individuals subjected to the intervention. In one embodiment, the surgical procedure is a severe surgical procedure. In another embodiment, the population of individuals subjected to the intervention is a control population or a randomized population. Pre-existing underlying disorders increase the risk that the patient will suffer from acute kidney injury following a surgical procedure. In one embodiment, the at-risk patient is a patient suffering from a cardiovascular disease and/or diabetes. In another embodiment, the patient suffers from cardiovascular atherosclerosis that requires treatment by coronary artery bypass surgery (CABP). In a patient suffering from cardiovascular atherosclerosis accompanying diseases, such as diabetes or cardiovascular disease, the risk of acute kidney injury increases. In one embodiment, the cardiovascular atherosclerosis accompanying disease is cardiovascular disease, and more particularly, heart failure or hypertension. In another embodiment, the cardiovascular atherosclerosis accompanying disease is diabetes, and more particularly, type 1 or type 2 diabetes. In one embodiment, the severity of the cardiovascular disease in patients in need of CABG is higher than in patients in need of other types of surgical procedures. In some embodiments, an increasing severity of the cardiovascular disease increases the risk of acute kidney injury after the surgical procedure. Except for the aforementioned specific diseases or conditions, the at-risk patient may appear to be apparently healthy.

The term "surgical procedure," as used herein, may refer to any surgical procedure that requires general anaesthesia and pulmonary or cardiopulmonary support. In some embodiments, the surgical procedure, which may be severe, is characterized by a duration of more than 30 minutes, or more than about 1, or more than about 2 hours. In certain embodiments, the surgical procedure is orthopedic surgery, a tumor resection, surgery of the gastrointestinal tract not involving tumor resection (e.g., the removal of diverticula), or cardiac surgery. In one embodiment, the surgical procedure is cardiac surgery, and more particularly, coronary artery bypass graft (CABG) surgery. CABG is indicated if a patient suffers from stenosis of the coronary arteries which cannot be treated successfully with other methods such percutaneous coronary intervention (PCI). This is typically the case if multiple vessels are affected or if the stenosis is not clearly localized. CABG is either performed "on-pump," i.e., the heart is stopped and does not beat during surgery, or "off-pump," i.e., the heart continues to beat during the procedure.

The term "acute kidney injury" or "AKI" refers to an impaired kidney function. AKI is characterized by an increase of serum creatinine of at least 0.3 mg/dl within 72 hours after surgery or by an increase of at least 50% from baseline. Typically, not all cases of AKI lead to functional impairment of the kidneys, which would require a renal replacement therapy. In severe cases of acute kidney injury, renal replacement therapy by hemodialysis to support the failing kidney function of the patient is required.

Acute kidney injury may occur during or immediately after the surgical procedure. In one embodiment, AKI begins during the surgical procedure or not later than 1, 2, or 3 days after surgery. Depending on the diagnostic method applied, it may only be recognizable several days after onset. In certain embodiments, acute kidney injury is not only temporally but also causally associated with the surgical procedure, i.e., the surgical procedure or its surrounding circumstances are the reason why the patient in question suffers from acute kidney injury.

The term "growth differentiation factor-15" or "GDF-15" relates to a polypeptide that is a member of the transforming growth factor (TGF)-β cytokine superfamily. The terms polypeptide, peptide, and protein are used interchangeably throughout this specification. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Hromas et al., 1997, *Biochim. Biophys. Acta* 1354(1): 40-44; Lawton et al., 1997, *Gene* 203(1): 17-26; Yokoyama-Kobayashi et al., 1997, *J. Biochem.* 122(30: 622-26; Paralkar et al., 1998, *J. Biol. Chem.* 273(22): 13760-67). Similar to other TGF-β-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kD dimeric protein (Bauskin et al., 2000, *EMBO J.* 19(10): 2212-20). Amino acid sequences and biological activities for GDF-15 are described in International Publication Nos. WO 99/06445, WO 00/70051, and WO 2005/113585; Böttner et al., 1999, *Gene* 237: 105-11; Baek et al., 2001, *Mol. Pharmacol.* 59(4): 901-08, Hromas et al., 1997; Paralkar et al., 1998; Morrish et al., 1996, *Placenta* 17(7): 431-41; Yokoyama-Kobayashi et al., 1997.

The term "troponin" refers to all troponin isoforms expressed in cells of the heart and subendocardial cells. These isoforms are well characterized in the art as described in, for example, Anderson et al., 1995, *Circ. Res.* 76(4): 681-86, and Ferrieres et al., 1998, *Clin. Chem.* 44(3): 487-93. In the disclosed methods, troponin may refer to troponin T and/or troponin I. Accordingly, both troponins may be determined in the method of the present disclosure together, i.e., simultaneously or sequentially, or individually, i.e., without determining the other isoform at all. Amino acid sequences for human troponin T and human troponin I are described in Anderson et al., 1995 and Ferrieres et al., 1998. The term "troponin" encompasses also variants of the aforementioned specific troponins, i.e., troponin T or troponin I.

The terms "GDF-15," "natriuretic peptide," and "troponin," as used herein, also encompass variants of the aforementioned specific polypeptides. Such variants have at least the same essential biological and immunological properties as the specific polypeptide of the present disclosure. In particular, they share the same essential biological and immunological properties if they are detectable by the same specific assays referred to in this specification, e.g., by ELISA assays using polyclonal or monoclonal antibodies specifically recognizing said polypeptides. Moreover, it is to be understood that a variant as referred to in the present disclosure shall have an amino acid sequence having at least one amino acid substitution, deletion, and/or addition wherein the amino acid sequence of the variant is still at least about 50%, at least about 60%, at least about 70%, at least about 80%, at least about 85%, at least about 90%, at least about 92%, at least about 95%, at least about 97%, at least about 98%, or at least about 99% identical to the amino sequence of the polypeptide of the present disclosure, over the entire length of the peptide. In the context of sequence identity of amino acid sequences or nucleic acid sequences, the term "at least about" refers to a sequence identity exceeding the indicated exact numerical value. The degree of identity between two amino acid sequences can be determined by algorithms well known in the art. In certain embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. Optimal alignment of sequences for comparison may be conducted by the local homology algorithm of Smith and Waterman, 1981, *Adv. Appl. Math.* 2: 482-89, by the homology alignment algorithm of Needleman and Wunsch, 1970, *J. Mol. Biol.* 48(3): 443-53, by the search for similarity method of Pearson and Lipman, 1988, *Proc. Natl. Acad. Sci. U.S.A.* 85(8): 2444-48, by computerized implementations of these algorithms (GAP, BESTFIT, BLAST, PASTA, and TFASTA in the Wisconsin Genetics Software Package, Genetics Computer Group (GCG), Madison, Wis.), or by visual inspection. Given that two sequences have been identified for comparison, GAP and BESTFIT may be employed to determine their optimal alignment and, thus, the degree of identity. In one embodiment, the default values of 5.00 for gap weight and 0.30 for gap weight length are used. Variants referred to above may be allelic variants or any other species-specific homologs, paralogs, or orthologs. Moreover, the variants referred to herein include fragments or subunits of the specific polypeptide or the aforementioned types of variants as long as these fragments have the essential immunological properties and/or biological activities as referred to above. Such fragments may be, e.g., degradation products of the polypeptides of the present disclosure. Also included are variants that differ due to posttranslational modifications such as phosphorylation or myristylation.

Determining the amount of GDF-15, a natriuretic peptide, troponin, or any other peptide or polypeptide referred to in this specification relates to measuring the amount or concentration. In certain embodiments, such measurements are semi-quantitative or quantitative. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, for example, by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present disclosure, determining the amount of a peptide or polypeptide can be achieved by all known means for determining the amount of a peptide in a sample. Said means comprise immunoassay devices and methods that may utilize labelled molecules in various sandwich, competition, or other assay formats. Said assays will develop a signal which is indicative for the presence or absence of the peptide or polypeptide. Moreover, the signal strength can be correlated directly or indirectly (e.g., reverse-proportional) to the amount of polypeptide present in a sample. Other suitable methods comprise measuring a physical or chemical property specific for the peptide or polypeptide such as its precise molecular mass or NMR spectrum. Said methods may comprise biosensors, optical devices coupled to immunoassays, biochips, and analytical devices such as mass-spectrometers, NMR-analyzers, or chromatography devices. Other suitable methods include micro-plate ELISA-based methods, fully-automated or robotic immunoassays (available, for example, on ELECSYS™ analyzers), CBA (an enzymatic Cobalt Binding Assay, available, for example, on ROCHE-HITACHI™ analyzers), and latex agglutination assays (available, for example, on ROCHE-HITACHI™ analyzers).

In one embodiment of the methods of the disclosure, the amount of a peptide or polypeptide is determined by contacting a cell capable of eliciting a cellular response, wherein the intensity is indicative of the amount of the peptide or polypeptide, with said peptide or polypeptide for an adequate period of time, and measuring the cellular response. For measuring cellular responses, the sample or processed sample can be added to a cell culture and an internal or external cellular response is measured. The cellular response may include the measurable expression of a reporter gene or the secretion of a substance, e.g., a peptide, polypeptide, or a small molecule. The expression or substance shall generate an intensity signal that correlates to the amount of the peptide or polypeptide.

In another embodiment of the methods of the disclosure, the amount of a peptide or polypeptide is determined by measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

In another embodiment of the methods of the disclosure, the amount of a peptide or polypeptide is determined by contacting the peptide with a specific ligand, optionally removing non-bound ligand, and measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Suitable ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well known in the art. For example, identification and production of suitable antibodies or aptamers is offered by commercial suppliers. Those skilled in the art are familiar with methods to develop derivatives of such ligands with higher affinity or specificity. For example, random mutations can be introduced into the nucleic acids, peptides, or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)$_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. In some embodiments, the ligand or agent specifically binds to the peptide or polypeptide. Specific binding according to the present disclosure means that the ligand or agent should not bind substantially to ("cross-react" with) another peptide, polypeptide, or substance present in the sample to be analyzed. In certain embodiments, the specifically bound peptide or polypeptide should be bound with at least 3 times higher, at least 10 times higher, or at least 50 times higher affinity than any other relevant peptide or polypeptide. Non-specific binding may be tolerable if it can still be distinguished and measured unequivocally, e.g., according to its size on a Western Blot, or by its relatively higher abundance in the sample. Binding of the ligand can be measured by any method known in the art. In certain embodiments, the method is semi-quantitative or quantitative. Suitable methods are described herein.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, the amount of substrate can be saturating. The substrate may also be labelled with a detectable label prior to the reaction. In one embodiment, the sample is contacted with the substrate for an adequate period of time. An adequate period of time refers to the time necessary for a detectable and measurable amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. Secondary, tertiary, or even higher order ligands are often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathione-S-transferase, FLAG, GFP, myc-tag, influenza A virus hemagglutinin (HA), maltose binding protein, and the like. In the case of a peptide or polypeptide, the tag may be located at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., magnetic beads, including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-START™ (Amersham Biosciences), ECF™ (Amersham Biosciences). A suitable enzyme-substrate combination may result in a colored reaction product, fluorescence, or chemoluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Other fluorescent labels are available e.g., from Molecular Probes (Oregon). Also the use of quantum dots as fluorescent labels is contemplated. Typical radioactive labels include $^{35}$S, $^{125}$I, $^{32}$P, $^{33}$P, and the like. A radioactive label can be detected by any method known and appropriate, e.g., a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Other methods known in the art (such as gel electrophoresis, 2D gel electrophoresis, SDS polyacrylamide gel electrophoresis (SDS-PAGE), Western Blotting, and mass spectrometry) can be used alone or in combination with labelling or other detection methods as described above.

The amount of a peptide or polypeptide may also be determined by contacting a solid support comprising a ligand for the peptide or polypeptide as specified above with a sample comprising the peptide or polypeptide and measuring the amount peptide or polypeptide which is bound to the support. The ligand may be chosen from the group consisting of nucleic acids, peptides, polypeptides, antibodies and aptamers, and can be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, and plastic tubes. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan et al., 2002, *Trends Biotechnol.* 20(1): 9-12). In such suspension arrays, the carrier, e.g., a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744,305).

The term "sample" refers to a sample of a body fluid, to a sample of separated cells or to a sample from a tissue or an organ. Samples of body fluids can be obtained by well known techniques and include, for example, samples of blood, plasma, serum, or urine. In certain embodiments of the disclosed methods, the sample is blood, plasma, or serum. Tissue or organ samples may be obtained from any tissue or organ by, e.g., biopsy. Separated cells may be obtained from the body fluids or the tissues or organs by separating techniques such as centrifugation or cell sorting. In some embodiments, cell, tissue, or organ samples are obtained from those cells, tissues, or organs that express or produce the peptides referred to herein. In one embodiment, the sample has been taken before the patient undergoes the surgical procedure, and in particular, the sample has been taken within 1 day before to 6 weeks before the surgical procedure is carried out. In certain embodiments, the sample is taken 1 or 2 days before the surgical procedure. In a stable patient, i.e., in a patient whose health status does not change, it may be desired to take the sample within 1 or 2 weeks before the surgical procedure. In an unstable patient the sample may be taken within 6 hours, 12 hours, or 24 hours before the surgical procedure.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. A comparison may be carried out manually or with the assistance of a computer. For a computer assisted comparison, the value of the determined amount may be compared to values corresponding to suitable references which are stored in a database by a computer program. The computer program may further evaluate the result of the comparison, i.e., automatically provide the desired assessment in a suitable output format. Based on the comparison of the amounts determined in step a) and the reference amount of the method of the present disclosure, it is possible to predict the risk of the patient suffering from one or more of the complications referred to herein. Therefore, the reference amount is to be chosen so that either a difference or a similarity in the compared amounts allows identifying those patients who are at risk of acute kidney injury after a surgical procedure.

Accordingly, the term "reference amount" as used herein refers to an amount which allows predicting whether a patient has an increased risk of acute kidney injury after a surgical procedure. Accordingly, the reference may either be derived from (i) a sample taken from a patient before being subjected to a surgery and known to have suffered from acute kidney injury afterwards or (ii) a sample taken from a patient before being subjected to a surgery and known to have not suffered from acute kidney injury after surgery. In one embodiment, the reference amount is determined on the basis of an averaged median amount obtained from a group of patients meeting the criteria either of (i) or of (ii), described above. Moreover, the reference amount may define a threshold amount, whereby an amount larger than the threshold shall be indicative for a subject that is at increased risk of AKI. The reference amount applicable for an individual subject may vary depending on various physiological parameters such as age, gender, or subpopulation, as well as on the means used for the determination of the polypeptide or peptide referred to herein. A suitable reference amount may be determined by the method of the present disclosure from a reference sample to be analyzed together, i.e., simultaneously or subsequently, with the test sample. In certain embodiments, the reference amount serving as a threshold may be derived from the upper limit of normal (ULN), i.e., the upper limit of the physiological amount to be found in samples from a population of subjects before being subjected to a surgery and who have not suffered or are not suffering from the complications as defined above, i.e., subjects known to have not suffered from acute kidney injury after surgery. The ULN for a given population of subjects can be determined by various well-known techniques. A suitable technique may be to determine the median or average of the population for the peptide or polypeptide amounts to be determined in the method of the present disclosure.

Reference amounts of a diagnostic marker (i.e., of GDF-15, a natriuretic peptide or troponin) can be established, and the level of the marker in a patient sample can simply be compared to the reference amount. The sensitivity and specificity of a diagnostic and/or prognostic test depends on more than just the analytical "quality" of the test—they also depend on the definition of what constitutes an abnormal result. In one embodiment, the distribution of the measured amounts of the markers of the present disclosure in a population of patients having suffered from acute kidney injury after a surgical procedure are compared to the distribution of the amounts of said marker in patients without said complications. In another embodiment, the distribution is determined in samples taken prior to surgery. Statistical methods well known to the person skilled in the art can be used to define a threshold amount that can be used to separate patients at risk of suffering from said complications and patients not at risk. A suitable statistical method for this purpose is the calculation of Receiver Operating Characteristic curves, or "ROC" curves. ROC-curves are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold may be selected above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., 1982, *Radiology* 143(1): 29-36.

In certain embodiments, markers (i.e., GDF-15, a natriuretic peptide or troponin) are selected to exhibit at least about 70% sensitivity, or at least about 80% sensitivity, or at least about 85% sensitivity, or at least about 90% sensitivity, or at least about 95% sensitivity, combined with at least about 70% specificity, or at least about 80% specificity, or at least about 85% specificity, or at least about 90% specificity, or at least about 95% specificity. In certain embodiments, both the sensitivity and specificity are at least about 75%, or at least about 80%, or at least about 85%, or at least about 90%, or at least about 95%.

In some embodiments of the disclosed methods, a pre-surgical amount of GDF-15 below about 1078 pg/ml rules out the risk of AKI after surgery, and a pre-surgical amount of GDF-15 above about 1717 pg/ml indicates an increased risk of AKI after surgery. In other embodiments, a pre-surgical amount of GDF-15 above about 2573 pg/ml indicates an increased risk of acute kidney injury requiring hemodialysis. Suitable threshold values of GDF-15 indicating a risk of AKI or AKI requiring hemodialysis based on the 75th percentiles, or for ruling out a risk of AKI or AKI requiring hemodialysis based on the 25th percentiles, are recited in Table 1a.

In some embodiments of the disclosed methods, a pre-surgical amount of troponin below about 7.7 pg/ml or about 13.3 pg/ml rules out the risk of AKI after surgery, and a pre-surgical amount of troponin above about 25.5 pg/ml or about 33.1 pg/ml indicates an increased risk of AKI after surgery. In other embodiments, a pre-surgical amount of troponin above about 60.9 pg/ml indicates an increased risk of acute kidney injury requiring hemodialysis. Suitable threshold values of troponin indicating a risk of AKI or AKI requiring hemodialysis based on the 75th percentiles, or for ruling out a risk of AKI or AKI requiring hemodialysis based on the 25th percentiles, are recited in Table 1 b.

In some embodiments of the disclosed methods, a pre-surgical amount of NT-proBNP below about 160.3 pg/ml or about 488.2 pg/ml rules out the risk of AKI after surgery, and a pre-surgical amount of NT-proBNP above about 1118.7 pg/ml or about 1385.5 pg/ml indicates an increased risk of AKI after surgery. In some embodiments, a pre-surgical amount of NT-proBNP above about 2227.1 pg/ml indicates an increased risk of acute kidney injury requiring hemodialysis. Suitable threshold values of NT-proBNP indicating a risk of AKI or AKI requiring hemodialysis based on the 75th percentiles, or for ruling out a risk of AKI or AKI requiring hemodialysis based on the 25th percentiles, are recited in Table 1c.

The term "about" is meant to indicate +/−30% of the indicated amount, or +/−20% of the indicated amount, or +/−10% of the indicated amount, or +/−5% of the indicated amount.

As set forth above, the reference amount may also be derived from a sample taken from a patient before being subjected to a surgery and known to have suffered from acute kidney injury afterwards. In some embodiments, an essentially identical or increased amount with respect to said reference amount of the biomarker GDF15, troponin and/or troponin indicates an increased risk of acute kidney injury after surgery. As set forth above, the reference amount may also be derived from a sample taken from a patient before being subjected to a surgery and known to have suffered from acute kidney injury and requiring hemodialysis afterwards. In some embodiments, an essentially identical or increased amount with respect to said reference amount of the biomarker GDF15 and/or troponin indicates an increased risk of AKI requiring hemodialysis after surgery.

Moreover, the reference amount may be obtained from a sample taken from a patient before being subjected to a surgery and known to have not suffered from acute kidney injury after surgery. In some embodiments, an essentially identical or decreased amount with respect to said reference amount of the biomarker GDF15 and/or troponin rules out the risk of AKI after surgery (and, thus, indicates that the risk is low).

Advantageously, the method of the present disclosure allows for the identification of patients with an increased risk of AKI prior to the surgical procedure. This is based on the surprising finding that the amounts of the markers of the present disclosure determined in a patient prior to the surgical procedure predict the risk of the patient suffering from acute kidney injury after the surgical procedure. From the determination of an increased risk of AKI in a patient practical consequences can be drawn immediately: known risk factors that precipitate AKI have to be controlled in a patient having an increased risk of acute kidney injury after a surgical procedure. Control of these risk factors includes careful fluid balance during and after surgery. If a cardiopulmonary bypass is used during surgery, low perfusion temperatures have to be avoided (Kourliouros et al., 2009). Nephrotoxic drugs (e.g., non steroidal anti-inflammatory drugs and sulfonamides) have to be avoided as well. Moreover, the administration of erythropoietin may be indicated (Song et al., 2009). The possibility to predict the risk of acute kidney injury after a surgical procedure in a patient prior to said intervention obviously has consequences for deciding whether the patient in question is eligible for the surgical procedure in question.

It will be understood that in another aspect of the method of the present disclosure, said method is a method for predicting in an at-risk patient who will be subjected to a surgical procedure the risk suffering from acute kidney injury comprising the step of comparing the amount of GDF-15 and/or troponin determined in a sample of the patient with a suitable reference amount as described herein to predict the risk of the patient suffering from acute kidney injury.

In one embodiment of the present disclosure the amount of a natriuretic peptide is determined in addition to the amount of GDF-15 and/or troponin.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present disclosure comprise ANP-type and BNP-type peptides and variants thereof (see, e.g., Bonow, 1996, *Circulation* 93(11): 1946-50). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Suitable natriuretic peptides for use in the disclosed methods are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in vivo half-life of NTproBNP is 120 min longer than that of BNP, which is 20 min. (Smith et al., 2000, *J. Endocrinol.* 167(2): 239-46). Preanalytics are more robust with NT-proBNP allowing easy transportation of the sample to a central laboratory (Mueller et al., 2004, *Clin. Chem. Lab. Med.* 42(8): 942-44). Blood samples can be stored at room temperature for several days or may be mailed or shipped without recovery loss. In contrast, storage of BNP for 48 hours at room temperature or at 4° Celsius leads to a concentration loss of at least 20% (Mueller et al., 2004; Wu et al., 2004, *Clin. Chem.* 50(5): 867-73). Therefore, depending on the time-course or properties of interest, either measurement of the active or the inactive forms of the natriuretic peptide can be advantageous. In certain embodiments, the natriuretic peptides are NT-proBNP or variants thereof. As briefly discussed above, the human NT-proBNP as referred to in the present disclosure is a polypeptide comprising 76 amino acids in length corresponding to the N-terminal portion of the human NT-proBNP molecule. The structure of the human BNP and NT-proBNP has been described already in detail in, e.g., International Publication Nos. WO 02/089657 and WO 02/083913; and Bonow 1996. In some embodiments, human NT-proBNP as used herein is human NT-proBNP as disclosed in European Patent No. EP 0 648 228 B1. These prior art documents are herewith incorporated by reference with respect to the specific sequences of NT-proBNP and variants thereof disclosed therein.

Moreover, it has been found in accordance with the present disclosure that the amount of GDF-15 after the surgical procedure is also indicative for an increased risk of acute kidney injury.

Therefore, the present disclosure contemplates also a method for predicting in an at-risk patient having been subjected to a surgical procedure the risk of acute kidney injury comprising the steps of determining the amount of GDF-15 in a sample of the patient; and comparing the determined amount with a reference amount, whereby the risk of acute kidney injury is predicted.

The explanations and definitions of the terms made above apply mutatis mutandis. It will be understood that for the disclosed methods, the sample has been taken after the surgical procedure has been completed, and in some embodiments, within a time window of not later than 1, 2, or 3 days after surgery. In other embodiments, the sample is taken immediately or not later than 1 day after completion of the intervention. In one such embodiment, the sample is taken immediately after surgery, wherein the term "immediately after surgery" refers to taking the sample not later than about 0.5 hours, not later than about 1 hour, not later than about 2 hours, not later than about 3 hours, or not later than about 6 hours after surgery. In one such embodiment, the sample is taken not later than 0.5 hours after surgery. The disclosed methods can be practiced after surgery to diagnose as early as possible, whether a patient having undergone a surgical procedure has an increased risk of acute kidney injury. In order to counter this risk effectively, therapeutic measures have to be taken as early as possible.

In one embodiment of the disclosed methods, the risk of AKI can be ruled out when the amount of GDF-15 in a sample taken immediately after surgery is below about 1807 pg/ml. In another embodiment, an amount of GDF-15 above about 3389 pg/ml indicates an increased risk of AKI after surgery. In still another embodiment, an amount of GDF-15 above about 6393 pg/ml indicates an increased risk of acute kidney injury requiring hemodialysis.

In one embodiment of the disclosed methods, the risk of AKI can be ruled out when the amount of GDF-15 in a sample taken 1 day after surgery is below about 6375 pg/ml. In another embodiment, an amount of GDF-15 above about 11988 pg/ml indicates an increased risk of AKI after surgery. In still another embodiment, an amount of GDF-15 above about 14507 pg/ml indicates, an increased risk of acute kidney injury requiring hemodialysis. Suitable threshold values of GDF-15 indicating a risk of AKI or AKI requiring hemodialysis based on the 75th percentiles, or for ruling out a risk of AKI or AKI requiring hemodialysis based on the 25th percentiles, are recited in Table 2a.

In one embodiment of the disclosed methods, the risk of AKI can be ruled out when the amount of GDF-15 in a sample taken 2 days after surgery is below about 2352 pg/ml. In another embodiment, an amount of GDF-15 above about 8034 pg/ml indicates an increased risk of AKI after surgery. In still another embodiment, an amount of GDF-15 above about 8929 pg/ml indicates an increased risk of acute kidney injury requiring hemodialysis. Suitable threshold values of GFD-15 indicating a risk of AKI or AKI requiring hemodialysis based on the 75th percentiles, or for ruling out a risk of AKI or AKI requiring hemodialysis based on the 25th percentiles, are recited in Table 2a.

In one embodiment of the disclosed methods, the risk of AKI can be ruled out when the amount of GDF-15 in a sample taken 3 days after surgery is below about 1903 pg/ml. In another embodiment, an amount of GDF-15 above about 4675 pg/ml indicates an increased risk of AKI after surgery. In still another embodiment, an amount of GDF-15 above about 5938 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2a.

In some embodiments of the disclosed methods, the risk of AKI can be ruled out when the amount of troponin in a sample taken immediately after surgery is below about 176.6 pg/ml or about 312.4 pg/ml. In other embodiments, an amount of troponin above about 503.6 pg/ml or about 593.1 pg/ml indicates an increased risk of AKI after surgery. In still other embodiments, an amount of troponin above about 640.3 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2b.

In some embodiments of the disclosed methods, the risk of AKI can be ruled out when the amount of troponin in a sample taken 1 day after surgery is below about 364.5 pg/ml or about 863.9 pg/ml. In other embodiments, an amount of troponin above about 1108.1 pg/ml or about 1217.3 pg/ml indicates an increased risk of AKI after surgery. In still other embodiments, an amount of troponin above about 1280.9 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2b.

In some embodiments of the disclosed methods, the risk of AKI can be ruled out when the amount of troponin In a sample taken 2 days after surgery is below about 279.5 pg/ml or about 537.6 pg/ml. In other embodiments, an amount of troponin above about 739.1 pg/ml or about 856.0 pg/ml indicates an increased risk of AKI after surgery. In still other embodiments, an amount of troponin above about 981.3 pg/ml or about 2006.1 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2b.

In some embodiments of the disclosed methods, the risk of AKI can be ruled out when the amount of troponin in a sample taken 3 days after surgery is below about 182.7 pg/ml or about 370.9 pg/ml. In other embodiments, an amount of troponin above about 492.6 pg/ml or about 812.5 pg/ml indicates an increased risk of AKI after surgery. In still other embodiments, an amount of troponin above about 575.0 pg/ml or about 1424.2 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2b.

In some embodiments of the disclosed methods, the risk of AKI can be ruled out when the amount of NT-proBNP in a sample taken immediately after surgery is below about 139.2 pg/ml or about 368.6 pg/ml. In other embodiments, an amount of NT-proBNP above about 924.6 pg/ml or about 940.3 pg/ml indicates an increased risk of AKI after surgery. In still other embodiments, an amount of NT-proBNP above about 1933.3 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2c.

In some embodiments of the disclosed methods, the risk of AKI can be ruled out when the amount of NT-proBNP in a sample taken 1 day after surgery is below about 914.1 pg/ml or about 1560.7 pg/ml. In other embodiments, an amount of NT-proBNP above about 1972.2 pg/ml or about 2565.1 pg/ml indicates an increased risk of AKI after surgery. In still other embodiments, an amount of NT-proBNP above about 3296.2 pg/ml or about 4876.7 pg/ml indicates, an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2c.

In some embodiments of the disclosed methods, the risk of AKI can be ruled out when the amount of NT-proBNP in a sample taken 2 days after surgery is below about 1667.0 pg/ml or about 2717.2 pg/ml. In other embodiments, an amount of NT-proBNP above about 4618.5 pg/ml or about 4953.2 pg/ml indicates an increased risk of AKI after surgery. In still other embodiments, an amount of NT-proBNP above about 6597.7 pg/ml indicates, an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2c.

In some embodiments of the disclosed methods, the risk of AKI can be ruled out when the amount of NT-proBNP in a sample taken 3 days after surgery is below about 1812.3 pg/ml or about 2825.0 pg/ml. In other embodiments, an amount of NT-proBNP above about 4983.7 pg/ml or about 5393.4 pg/ml indicates an increased risk of AKI after surgery. In still other embodiments, an amount of NT-proBNP above about 5291.9 pg/ml indicates an increased risk of acute kidney injury requiring hemodialysis. Suitable threshold values indicating a risk of AKI or AKI requiring hemodialysis based on the 75th percentiles, or for ruling out a risk of AKI or AKI requiring hemodialysis based on the 25th percentiles, are recited in Table 2c.

The disclosed methods can also be applied for predicting whether a patient is in need of renal replacement therapy including hemodialysis, or for predicting a patient's mortality risk, or in certain embodiments, for predicting an increased mortality risk for a patient.

In one embodiment of the disclosed methods, the risk of acute kidney injury in an at-risk patient who has been subjected to a surgical procedure is predicted by comparing the amount of GDF-15 determined in a sample obtained from the patient with a suitable reference amount as described herein to predict the risk of acute kidney injury.

In other embodiments of the disclosed methods, the amount of a natriuretic peptide and/or troponin is determined in addition to the amount of GDF-15.

The present disclosure also relates to a method for facilitating a surgical decision in an at-risk patient, comprising the steps of determining the amount of GDF-15 and/or troponin in a sample obtained from the patient; and comparing the amount GDF-15 and/or troponin in the sample with a suitable reference amount, wherein the amount of GDF-15 and/or troponin in the sample indicates whether the patient should undergo the surgical procedure.

For each individual patient, the potential benefits of a surgical procedure have to be balanced against the potential side effects of that procedure. One potential side effect is acute kidney injury. Because the disclosed methods allow for a risk prediction on an individual basis, the decision about whether a patient should undergo a surgical procedure can be made based on the specific needs and risks of the patient. Accordingly, the phrase "facilitating a surgical decision in an at-risk patient," means to make a risk stratification as described above, to balance the risk and the benefit of the surgical procedure and to assist in providing a recommendation for carrying out the procedure.

In one embodiment of the disclosed methods, the surgical procedure is coronary artery bypass graft surgery. While CABG improves the quality of life of patients, it does not lead to prolonged survival (Eagle et al., 1999, *J. Am. Coll.*

*Cardiol.* 34(4): 1262-347). Thus, in the case of planned CABG, the potentially lethal consequences of AKI have to be balanced against the potentially improved quality of life after CABG.

Some patients who are at risk of AKI following surgery are not ideal candidates for a surgical procedure. In such patients, the decision about performing the surgical procedure can be based on the reference amounts of GDF-15 and/or troponin described herein.

In one embodiment of the disclosed methods, a surgical decision in an at-risk patient is facilitated by comparing the amount of GDF-15 and/or troponin in a sample obtained from the patient with a suitable reference amount as described herein, to facilitate the surgical decision.

In one embodiment of the disclosed methods, the amount of a natriuretic peptide is determined in addition to the amount of GDF-15 and/or troponin.

The present disclosure also relates to the use of the biomarker GDF15 and/or troponin in a sample of a patient who will be subjected to a surgical procedure for predicting the risk of acute kidney injury.

Moreover, the present disclosure relates to the use of a detection agent that specifically binds to GDF15 and/or of a detection agent that specifically binds to troponin in a sample of a patient who will be subjected to a surgical procedure for predicting the risk of acute kidney injury.

Also, the present disclosure relates to the use of the biomarker GDF15 and/or a troponin in a sample of an at-risk patient for deciding whether said patient is eligible for a surgical procedure.

Moreover, the present disclosure relates to the use of a detection agent that specifically binds to GDF15 and/or a detection agent that specifically binds to troponin in a sample obtained from an at-risk patient for deciding whether the patient should undergo a surgical procedure.

Moreover, the present disclosure relates to the use of a detection agent that specifically binds GDF15 in a sample obtained from an at-risk patient having been subjected to a surgical procedure for predicting the risk of acute kidney injury.

The term "detection agent," as used herein, refers to an agent which is capable of specifically recognizing and binding to one of the biomarkers referred to herein when present in a sample. Moreover, the detection agent shall allow for direct or indirect detection of the complex formed by the detection agent and the biomarker. Direct detection can be achieved by incorporating a detectable label in the detection agent. Indirect labelling may be achieved by using a second agent that specifically binds to a complex comprising the biomarker and the detection agent, wherein the second agent is than capable of generating a detectable signal. Suitable compounds for use as detection agents are well known in the art. In some embodiments of the disclosed methods, the detection agent is an antibody (e.g., a monoclonal or a polyclonal antibody) or aptamer that specifically binds to the biomarker.

Furthermore, the present disclosure relates to a device for predicting the risk of acute kidney injury in an at-risk patient subjected to a surgical procedure, comprising an analyzing unit for determining the amount of GDF-15 and/or troponin in a sample obtained from the patient; and an evaluation unit for comparing the determined amount with a suitable reference amount and for predicting the risk of acute kidney damage.

The term "device" as used herein relates to a system comprising at least the aforementioned means operatively linked to each other as to practice the method of the present disclosure. Suitable means for determining the amounts of the markers of the disclosed methods, and means for carrying out the comparison are disclosed above in connection with the disclosed methods. How to link the means in an operating manner will depend on the type of means included in the device. For example, where an analysis unit for automatically determining the amount of the gene products of the present disclosure is applied, the data obtained by said automatically operating analysis unit can be processed by, e.g., a computer as evaluation unit in order to obtain the desired results. In some embodiments, the means are comprised of a single device in such a case.

Suitable reference amounts are described herein.

In some embodiments, the device for predicting the risk of AKI in an at-risk patient includes an analyzing unit for the measurement of the amount of GDF-15/and or troponin in an applied sample and an evaluation unit for processing the resulting data. In certain embodiments, the evaluation unit comprises a database with the stored reference amounts and a computer program code which when tangibly embedded on a computer carries out the comparison of the determined amounts and the reference amounts stored in the database. In other embodiments, the evaluation unit comprises a further computer program code that allocates the result of the comparison to a risk prediction. In such a case, it is envisaged that the evaluation unit comprises a further database wherein the reference amounts are allocated to the risks.

Alternatively, where means such as test strips are used for determining the amount of GDF-15 and/or troponin, the evaluation unit may comprise control strips or tables allocating the determined amount to a reference amount. In some embodiments, the test strips are coupled to ligands that specifically bind to GDF-15 and/or troponin. In other embodiments, the strip or device comprises means for detection of the binding of GDF-15 and/or troponin to said ligands. Suitable means for detection are disclosed in connection with embodiments relating to the disclosed methods. In such a case, the analysis unit and the evaluation unit are operatively linked in that the user of the system brings together the result of the determination of the amount and the diagnostic or prognostic value thereof due to the instructions and interpretations given in a manual. The analysis unit and the evaluation unit may appear as separate devices in such an embodiment, and in some embodiments are packaged together as a kit. A person skilled in the art will realize how to link the means. Suitable devices are those that can be applied without the particular knowledge of a specialized clinician, e.g., test strips or electronic devices that merely require loading with a sample. The results may be given as output of raw data, which need interpretation by the clinician. In certain embodiments, however, the output of the device is processed, i.e., evaluated, raw data that does not require interpretation by a clinician. Other suitable devices comprise the analyzing units/devices (e.g., biosensors, arrays, solid supports coupled to ligands specifically recognizing the gene product, plasmon surface resonance devices, NMR spectrometers, or mass-spectrometers) or evaluation units/devices referred to above in accordance with the methods of the disclosure.

Moreover, the present disclosure relates to a kit for predicting the risk of acute kidney injury in an at-risk patient subjected to a surgical procedure, comprising an analyzing agent for determining the amount of GDF-15 and/or troponin in a sample obtained from the patient; and an evaluation unit for comparing the amounts determined by the analyzing agent with a suitable reference amount, said unit further allowing the prediction of the risk of acute kidney damage The term "kit" as used herein refers to a collection of the aforementioned components that may or may not be packaged together. The components of the kit may be comprised by separate vials (i.e., as a kit of separate parts) or provided in a single vial. Moreover, it is to be understood that the kit of the present disclosure is to be used for practicing the methods referred to herein. In some embodiments, it is envisaged that all components are provided in a ready-to-use manner for practicing the methods referred to above. In certain embodiments, the kit also contains instructions for carrying out the disclosed methods. The instructions can be provided by a user's manual in paper or electronic form. For example, the manual may comprise instructions for interpreting the results obtained when carrying out the aforementioned methods using the kit of the present disclosure. The kit shall comprise an analyzing agent. This agent is capable of specifically recognizing GDF-15 and/or troponin in a sample obtained from the patient. Moreover, in some embodiments, the agent(s) shall, upon binding to the GDF-15 and/or troponin, be capable of generating a detectable signal, the intensity of which correlates to the amount of GDF-15 and/or troponin present in the sample. Depending on the type of signal that is generated, methods for detection of the signal can be applied which are well known in the art. Analyzing agents that can be used for the kit of the present disclosure include antibodies or aptamers. The analyzing agent may be present on a test strip as described herein. The amounts of GDF-15 and/or troponin detected can then be further evaluated in the evaluation unit. Suitable evaluation units to be used for the kit of the present disclosure include those referred to herein.

In another embodiment, the disclosed methods relate to a method for diagnosing myocardial infarction (MI) in a patient, and more particularly, an at-risk patient, comprising the steps of determining the amount of troponin T in a sample of the patient; comparing the measured amount of troponin T to a suitable reference amount; and diagnosing whether said patient suffers from MI based on such comparison.

Moreover, in yet another embodiment, the disclosed methods are carried out by determining TGF-ß instead of GDF-15.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Example 1. Patients, Materials and Methods

A total of 126 patients undergoing coronary artery bypass graft (CABG) surgery were included in the study. There were 68 males and 58 females in the study group, which ranged in age from 52 to 81 years and had a median age of 68 years. Serum creatinine levels were normal in all patients. All patients were found to have two or more vessel disease as indicated by at least one stenosis exceeding 50% of the lumen. Patients were followed for 30 days with respect to mortality and development of acute kidney injury. Endpoints of the study were: acute kidney injury (AKI; creatinine increase at least 0.3 mg/dl within 3 days after surgery), new requirement for hemodialysis, or mortality (within 30 days after surgery). Blood was taken before surgery and immediately thereafter as well as at 1, 2, and 3 days after surgery. Samples were centrifuged for 30 minutes and stored at −20° C. until analyzed.

GDF-15, troponin T, and NT-proBNP were determined with sandwich immunoassays using COBAS-analyzers from Roche/Hitachi. The assays comprise two monoclonal antibodies specific for the respective polypeptide. The first of these is biotinylated and the second one is labelled with a Tris(2,2'-bipyridyl)ruthenium(II)-complex. In a first incubation step, both antibodies were incubated with a patient sample, forming a sandwich complex comprising the peptide to be assayed and the two different antibodies. In a next incubation step, streptavidin-coated beads were added to the sandwich complex from the first incubation step, allowing the beads to bind to the sandwich complexes. The reaction mixture was then aspirated into a measuring cell where the beads were magnetically captured on the surface of an electrode. The application of a voltage induced a chemiluminescent emission from the ruthenium complex, which was measured by a photomultiplier, the amount of emitted light being dependent on the amount of sandwich complexes that were captured on the electrode. In the sandwich immunoassays described above, GDF-15 amounts between 300 pg/ml to 20000 pg/ml, troponin T amounts between 3 pg/ml to 10000 pg/ml, and NT-proBNP amounts between 5 pg/ml and 35000 pg/ml could be measured.

Creatinine was determined using a modification of the Jaffe method (Foster-Swanson et al., 1994, *Clin. Chem.* Abstract #361; Seelig and Wüst, 1969, *Arztliches Labor* 15: 34-39; Bartels et al., 1972, *Clin. Chim. Acta* 37: 193-97). Briefly, picrinic acid was allowed to react with creatinine in alkaline solution to form a yellow-orange complex. The complex was detected photometrically using Roche/Hitachi analyzers.

The results obtained in this study are shown in Tables 1a to 1c and 2a to 2c below.

TABLE 1a

GDF-15 levels before surgery

| Outcome | No AKI | AKI | Dialysis | Mortality |
|---|---|---|---|---|
| N | 89 | 37 | 12 | 9 |
| Median GDF-15 [pg/ml] | 1078 | 1717 | 2573 | 2442 |
| 25th percentile [pg/ml] | 781 | 1101 | 1250 | 1626 |
| 75th percentile [pg/ml] | 1401 | 2448 | 4508 | 3273 |

TABLE 1b

Troponin T levels before surgery

| Outcome | No AKI | AKI | Dialysis |
|---|---|---|---|
| N | 89 | 37 | 12 |
| Median TnT [pg/ml] | 13.34 | 25.52 | 60.89 |

TABLE 1b-continued

Troponin T levels before surgery

| Outcome | No AKI | AKI | Dialysis |
|---|---|---|---|
| 25th percentile [pg/ml] | 7.67 | 16.54 | 23.20 |
| 75th percentile [pg/ml] | 33.11 | 62.01 | 495.97 |

TABLE 1c

NT-proBNP levels before surgery

| Outcome | No AKI | AKI | Dialysis |
|---|---|---|---|
| N | 89 | 37 | 12 |
| Median NT-proBNP [pg/ml] | 488.18 | 1385.49 | 2227.06 |
| 25th percentile [pg/ml] | 160.26 | 481.45 | 794.08 |
| 75th percentile [pg/ml] | 1118.66 | 2485.66 | 3358.61 |

As shown in Tables 1a to 1c, the group of patients who suffer from AKI after CABP were found to have increased median amounts of GDF-15, troponin T, and NT-proBNP. In addition, the median amounts of GDF-15, troponin T, and NT-proBNP before surgery were found to be higher in patients suffering from a severe case of AKI (requiring hemodialysis) after surgery. Thus, GDF-15, troponin T, and NT-proBNP can be used to predict and differentiate between different severities of AKI.

TABLE 2a

GDF-15 levels [pg/ml] at different time points after surgery

| | No AKI* | AKI* | Dialysis* | Mortality* |
|---|---|---|---|---|
| Immediately after surgery | 1807 1337-3467 | 3389 2036-6584 | 6393 3571-7653 | 5256 3401-8099 |
| 1 day after surgery | 6375 4177-8603 | 11988 8393-20600 | 14507 9525-22230 | 9786 8605-14260 |
| 2 days after surgery | 2352 1619-3201 | 8034 3985-11748 | 8929 5233-13038 | 8930 5087-13774 |
| 3 days after surgery | 1903 1487-3033 | 4675 3397-7731 | 5938 4366-11022 | 5652 4150-8408 |

*Median values, 25th and 75th percentiles

TABLE 2b

Troponin T levels [pg/ml] at different time points after surgery

| | No AKI* | AKI* | Dialysis* |
|---|---|---|---|
| Immediately after surgery | 312.39 176.63-503.56 | 593.14 139.87-1908.04 | 640.34 549.87-1421.68 |
| 1 day after surgery | 863.85 364.48-1217.33 | 1108.10 448.83-3612.46 | 1280.91 500.98-5439.78 |
| 2 days after surgery | 537.61 279.53-855.98 | 739.07 387.11-2074.96 | 981.30 357.56-2006.06 |
| 3 days after surgery | 370.92 182.70-812.45 | 492.60 310.91-1424.18 | 574.96 315.58-1724.62 |

*Median values, 25th and 75th percentiles

TABLE 2c

NT-proBNP levels [pg/ml] at different time points after surgery

| | No AKI* | AKI* | Dialysis* |
|---|---|---|---|
| Immediately after surgery | 368.58 139.15-940.25 | 924.62 381.57-2124.55 | 1933.30 914.53-5824.65 |
| 1 day after surgery | 1560.68 914.09-2565.12 | 1972.22 1086.06-4686.00 | 4876.65 3296.20-6485.33 |
| 2 days after surgery | 2717.21 1667.04-4618.54 | 4953.24 2344.10-10839.93 | 6597.74 2978.74-13846.26 |
| 3 days after surgery | 2825.03 1812.31-5393.36 | 4983.66 2661.26-9243.66 | 5291.93 4092.11-12000.25 |

*Median values, 25th and 75th percentiles

As shown in Table 2a to 2c, patients likely to experience complications following cardiovascular surgery can also be identified. Patients suffering from a severe case of AKI requiring hemodialysis were found to have generally higher levels of GDF-15, troponin T, and NT-proBNP than patients who suffered from AKI without the need for hemodialysis. Thus, GDF-15, troponin T, and NT-proBNP can be used to not only predict the occurrence of AKI but also the severity of AKI.

Example 2. Individual Patient Cases

Case 1: a 62-year-old male, suffering from 3-vessel disease with multiple stenoses, underwent CABG. He had long-standing arterial hypertension, no diabetes mellitus or smoking history. His lipids were in the normal range. However, this patient had a history of obesity. The following results were obtained for this patient before and after surgery:

| | before surgery | after surgery | 1 day after surgery | 2 days after surgery | 3 days after surgery |
|---|---|---|---|---|---|
| Creatinine [mg/dl] | 0.80 | 0.72 | 0.90 | 0.81 | 0.84 |
| GDF-15 [pg/ml] | 1700 | 1800 | 5600 | 2900 | 1900 |
| TnT [pg/ml] | 12.9 | 316.0 | 582.0 | 416.0 | 352.0 |
| NT-proBNP [pg/ml] | 380 | 410 | 1420 | 1530 | 1380 |

The patient recovered from CABG without further complications, with no occurrence of AKI. Before surgery, the amounts of GDF-15 and NT-proBNP were below the reference amount that would indicate an increased risk of AKI post surgery (1717 pg/ml and 1119 pg/ml, respectively). In addition, the amount of troponin T indicated that an increased risk of AKI could be ruled out (TnT below 13.3 pg/ml).

Case 2: a 58-year-old male, suffering from 2-vessel disease with multiple stenoses, underwent CABG. He was a previous smoker, had arterial hypertension and no diabetes mellitus. His lipids were in the normal range. The following results were obtained for this patient before and after surgery:

|  | before surgery | after surgery | 1 day after surgery | 2 days after surgery | 3 days after surgery |
|---|---|---|---|---|---|
| Creatinine [mg/dl] | 1.15 | 1.08 | 1.40 | 2.1 | 1.6 |
| GDF-15 [pg/ml] | 3200 | 3300 | 10000 | 13000 | 4100 |
| TnT [pg/ml] | 23.9 | 621.0 | 490.0 | 380.0 | 210.0 |
| NT-proBNP [pg/ml] | 1480 | 2010 | 3860 | 3540 | 3790 |

The patient experienced acute kidney injury, but recovered spontaneously without need for acute dialysis. Before surgery, the amount of GDF-15 indicated an increased risk of AKI requiring renal replacement therapy, the amount of troponin T was just below the threshold indicating an increased risk of AKI (25.5 pg/ml), and the amount of NT-proBNP indicated an increased risk of AKI. Taken together, two out of three markers indicated the presence of an increased risk of AKI. In addition, the necessity of hemodialysis was predicted for one marker. The occurrence of AKI in this patient, therefore, conformed with the prediction.

Case 3: a 62-year-old male suffering from extensive 3 vessel disease underwent CABG. He had dyspnoe before surgery and reported episodes of symptomatic heart failure in the past that were treated with ACE-inhibitors, beta-blockers, and diuretics. His kidney function was marginal and changed with the use of loop diuretics. His risk profile included smoking, arterial hypertension, and obesity, but had recently lost weight. The following results were obtained before and after surgery:

|  | before surgery | after surgery | 1 day after surgery | 2 days after surgery | 3 days after surgery |
|---|---|---|---|---|---|
| Creatinine [mg/dl] | 1.2 | 1.3 | 1.6 | 3.2 | 4.5 |
| GDF-15 [pg/ml] | 2416 | 5820 | 9210 | 8760 | 5820 |
| TnT [pg/ml] | 62.3 | 657.0 | 1380.0 | 975.0 | 612.0 |
| NT-proBNP [pg/ml] | 2480 | 1980 | 4920 | 6370 | 5910 |

The patient suffered from AKI post surgery and required hemodialysis. Before surgery, the amounts of troponin T and NT-proBNP indicated an increased risk of AKI requiring hemodialysis, and the amount of GDF-15 was just below the reference value indicating the risk of AKI requiring hemodialysis (2573 pg/ml). Hence, all three markers correctly predicted the occurrence of AKI, and two of the markers also correctly predicted a severe case of AKI requiring hemodialysis.

All publications, patents, and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

The invention claimed is:

1. A method for treating a patient at risk of developing acute kidney injury (AKI) after coronary artery bypass graft (CABG) surgery, the method comprising:
   identifying a patient as being at high risk of developing AKI after CABG surgery,
   wherein the patient is identified by:
   (a) determining the amount of a biomarker in a plasma or serum sample from the patient which has been taken within 1 week or 2 weeks before the patient undergoes CABG surgery, wherein the biomarker comprises GDF-15 and/or Troponin; and
   (b) comparing the determined amount of the biomarker with a reference amount suitable for predicting whether a patient is at high risk of developing AKI after CABG surgery;
   wherein the amount of GDF-15 is increased compared to a reference amount of GDF-15 and/or the amount of Troponin is increased compared to a reference amount of Troponin in a patient at high risk of developing AKI; and
   administering a drug to the patient identified as being at high risk of developing AKI after CABG surgery.

2. The method of claim 1, wherein the Troponin is Troponin T.

3. The method of claim 1, wherein additionally the amount of a natriuretic peptide is determined and compared to a reference amount of the natriuretic peptide.

4. The method of claim 3, wherein the natriuretic peptide is NT-proBNP.

5. The method of claim 1, wherein the sample is taken within 6 hours, 12 hours or 24 hours before the surgical procedure.

6. The method of claim 1, wherein the reference amount is an averaged median amount obtained from a group of patients before being subjected to surgery, and wherein the group of patients did not suffer from AKI after surgery.

7. The method of claim 1, wherein the patient suffers from a cardiovascular disease.

8. The method of claim 7, wherein the patient suffers from cardiovascular artherosclerosis.

9. The method of claim 1, wherein the drug is erythropoietin.

* * * * *